United States Patent [19]

Gronauer

[11] Patent Number: 5,472,423
[45] Date of Patent: Dec. 5, 1995

[54] FLEXIBLE CATHETER

[76] Inventor: Volker Gronauer, Römerbrunnenweg 38, 91781 Weissenburg, Germany

[21] Appl. No.: 191,382

[22] Filed: Feb. 3, 1994

[30] Foreign Application Priority Data

Feb. 5, 1993 [DE] Germany .................... 9301616 U

[51] Int. Cl.$^6$ ..................................... A61N 5/02
[52] U.S. Cl. ............................................ 604/96
[58] Field of Search .................. 604/96, 101, 280, 604/281–284, 264–266; 606/191–194

[56] References Cited

U.S. PATENT DOCUMENTS 2,548,602  4/1951  Greenburg ........................... 604/96
5,129,396  7/1992  Rosen et al. ...................... 128/653.1
5,150,717  9/1992  Rosen et al. ....................... 128/804
5,158,540  10/1992 Wijay et al. .......................... 604/96
5,275,597  1/1994  Higgins et al. ....................... 606/33

FOREIGN PATENT DOCUMENTS 2728636  6/1977  Germany .

Primary Examiner—C. Fred Rosenbaum
Assistant Examiner—Manuel Mendez
Attorney, Agent, or Firm—Dena Meyer Weker; Wayne D. House

[57]  ABSTRACT

A flexible catheter is provided for use with an antenna which radiates high-frequency or microwave energy, the catheter having a carrier tube and an outer layer of microporous polytetrafluoroethylene on the outer circumference of the carrier tube.

6 Claims, 1 Drawing Sheet

FLEXIBLE CATHETER

FIELD OF THE INVENTION

A flexible catheter is provided for use with an antenna which radiates high-frequency or microwave energy having a carrier tube and an outer layer of microporous polytetrafluoroethylene (PTFE) on the outer circumference of the carrier tube. The invention is particularly useful in medical applications.

BACKGROUND OF THE INVENTION

Catheters are widely used in medical applications. They have been particularly useful in treating an enlarged prostate by microwave treatment. For this application, a catheter is inserted into the urethra of the man to be treated until an inflatable balloon, which is located at the front insertion end of the catheter, is positioned in the urinary bladder. The balloon is then inflated and held stationary within the bladder. Subsequently, a microwave antenna is inserted through an inner lumen of the catheter until it is located adjacent to the prostate. The antenna is arranged at the front end of an antenna cable, while the other end of the cable, which protrudes from the catheter, is connected with a microwave energy source.

In the vicinity of the bladder the urethra has a relatively sharp bend. The catheter must be highly flexible and easily bendable.

Since the microwave antenna is located within the catheter, the microwave energy must be radiated through the catheter wall to the prostate. Not all materials are suitable for construction of the catheter.

A conventional catheter for the microwave treatment of the prostate uses a multi-lumen catheter tube made of polyvinylchloride (PVC). Such a PVC catheter is highly flexible but not satisfactory from an electrical point of view. PVC excessively attenuates microwaves and therefore heats up. As a consequence, the catheter tube softens and the surrounding body tissue is subjected to undesirable heat.

DE2728636 C2 describes a small tube for medical endoscopes, in particular gastroscopes, with a 3-layer construction comprising an impermeable intermediate layer, an outer layer and an inner layer. The outer layer and the inner layer consist of a porous polymerisate with fibril structure, for instance porous polytetrafluoroethylene (PTFE). The intermediate layer may consist of a flexible metal film or a thin flexible plastic material such as fluorinated ethylene propylene (FEP), copolymer, perfluoroalkoxy resin (PFA) or polyvinylchloride (PVC). A flexible metal film makes this small existing tube unsuitable for any use as a catheter for inserting an antenna which radiates microwave energy. The metal film completely shields off the microwave energy. The proposed use of plastic materials, such as PVC, for the small known tube, is unsuitable because it has too strong an attenuation for the microwave energy, (i.e. absorbs too much microwave energy).

There is a need to provide a flexible catheter that is easily bendable but maintains desirable electrical and attenuation properties.

SUMMARY OF THE INVENTION

A flexible medical catheter is provided for use as an insertion device with an antenna which radiates high-frequency energy such as microwave energy comprising a carrier tube having an outer circumference, the carrier tube made of polytetrafluoroethylene (i.e. not microporous), and an outer layer which covers the outer circumference of the carrier tube, the outer layer made of microporous polytetrafluoroethylene. The catheter further is provided with a carrier tube that has a double wall structure with an outer tube and a concentric inner tube which are connected with each other by means of radial bridging elements that are uniformly distributed around the circumference so that an inner lumen is formed within the inner tube for insertion of the antenna and several other luminae are formed between the inner tube and outer tube.

DETAILED DESCRIPTION OF THE PREFERRED EMBODIMENTS

A medical catheter is provided for use with an antenna which radiates high-frequency and microwave energy comprising a carrier tube and an outer layer which covers the outer circumference of the carrier tube.

The carrier tube of the catheter is comprised of polytetrafluoroethylene (PTFE). This non-porous polymer possesses excellent electrical properties.

PTFE is a dielectric which is very well suited for microwave radiation. It has minimum attenuation of microwave energy. This prevents buildup of heat and the subsequent softening of the catheter due to the radiation of microwave energy through the catheter material. The reduced heat load also reduces the heating up of the body so that less cooling water is required. Additionally, the antenna needs to be supplied with less microwave energy.

Polytetrafluoroethylene (which has not been processed to make a porous microstructure) is less flexible than the conventionally used PVC. The required flexibility is provided by having a carrier tube that is thinner than conventional PVC catheter tubes. Typically, a PVC catheter tube has a wall thickness of between 0.2 and 0.3 mm. To the contrary, a PTFE tube has a wall thickness of about 0.1 mm. The residual thickness of the catheter tube is achieved through the outer layer which consists of microporous PTFE.

Microporous, expanded PTFE is described in the U.S. Pat. Nos. 3,953,566 and 4,187,390. It also has very good electrical characteristics. The outer catheter layer consisting of microporous PTFE has good padding properties. This is advantageous when the catheter is moved through bends of the urethra. Furthermore, microporous PTFE has very good sliding properties.

The outer layer of the catheter may be made from a tape of microporous PTFE which is wrapped around the carrier tube, or a separate tube of microporous PTFE which is applied over the carrier tube or may be extruded onto the carrier tube, either simultaneously or subsequently.

The construction of the device is best understood by referring to the accompanying drawings.

Figure 1:
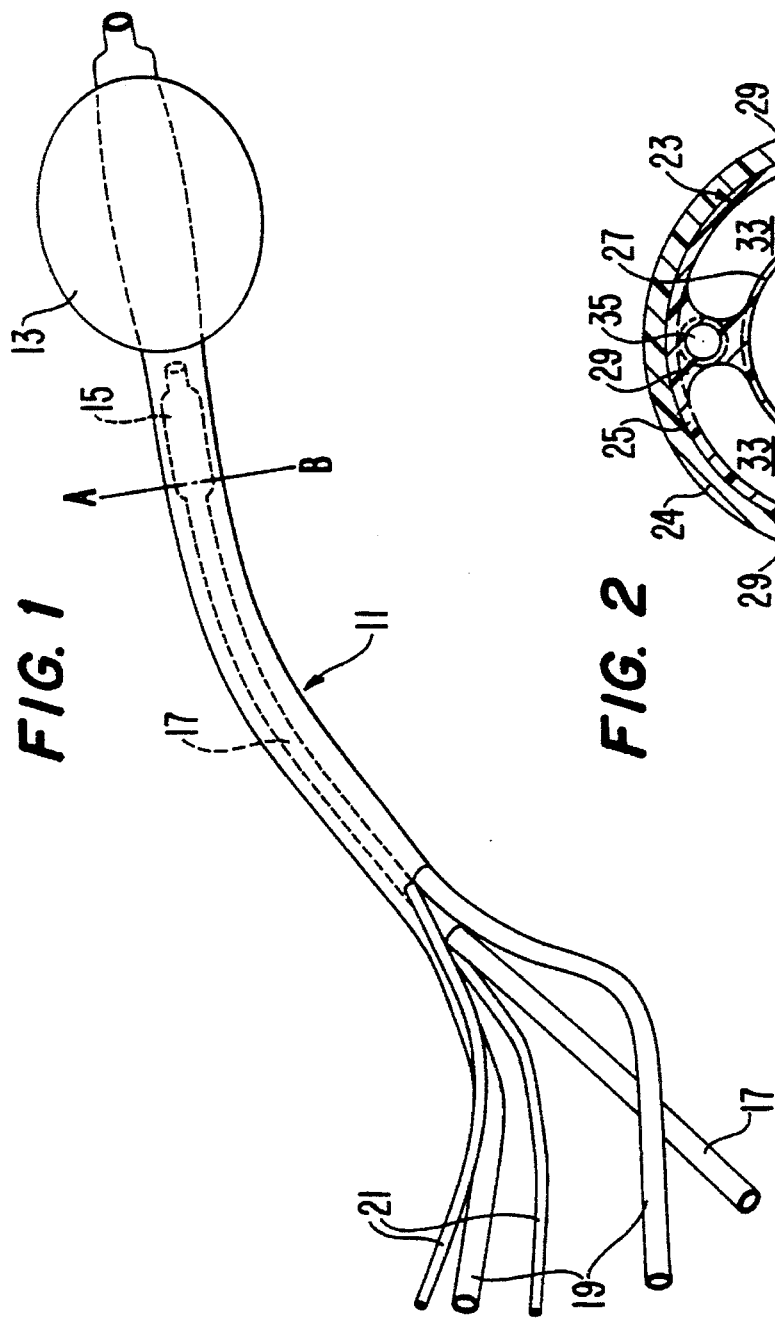
FIG. 1 is a schematic view of a catheter for prostate microwave treatment.

FIG. 1 is a schematic view of a catheter 11 which can be inserted into the urethra. At the end of the catheter which is inserted first, there is an inflatable balloon 13 which is shown in the inflated state in FIG. 1. A microwave antenna 15 is inserted into the catheter at the end of the microwave cable 17. At the end of the catheter 11 opposite to the insertion end, a microwave cable 17, two cooling water tubes 19 and two sensor lines 21 are guided into the catheter 11.

Figure 2:
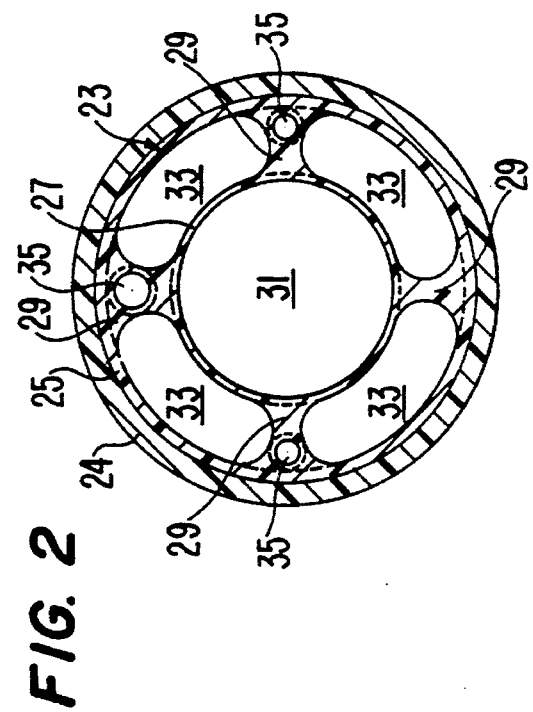
FIG. 2 is a cross-section of the catheter of FIG. 1.

FIG. 2 is a cross-section of the catheter 11 across line A–B of FIG. 1. The catheter has a circular cross-section in the preferred embodiment. Catheter 11 comprises a carrier tube 23 made from PTFE on whose outer circumference there is a tubular outer layer 24 which consists of microporous PTFE. The carrier tube is provided with an outer tube 25 and a concentrical inner tube 27.

The outer tube 25 and the inner tube 27 are connected with each other via several radial bridging elements 29 also made of PTFE which are uniformly distributed around the circumference of the carrier tube 23—the figure shows four such bridging elements. An inner lumen 31 is formed within the inner tube 27 and can accommodate the microwave antenna 15 and the microwave line 17. Four outer lumenae 33 are formed between the radial bridging elements 29. These are utilized for the supply and discharge of cooling water. Bridging lumenae 35 are formed in three of the four radial bridging elements 29. Two of them serve to insert measuring or monitoring sensors. The bridging lumen 35 shown on top of FIG. 2 serves as a supply of inflation fluid, such as air to inflate the balloon 13.

The radial bridging elements 29 impart a high mechanical strength to the outer tube 25 and the entire catheter 11 so that the individual lumenae are protected against indentations and squeezing. The outer layer 24 consists of microporous PTFE and not only has good padding, sliding and electrical properties, but also compensates for crushing effects which may occur after sharp bending of the catheter 11 so that no wrinkles are formed on the outer circumference of the catheter 11.

I claim:

1. A flexible medical catheter for use with an inflatable balloon and an antenna which radiates high-frequency, said catheter comprising:

a) a carrier tube of polytetrafluoroethylene and having an outer circumference; and b) an outer layer which covers the outer circumference of the carrier tube, said outer layer made from porous polytetrafluoroethylene.

2. A flexible medical catheter of claim 1 wherein the carrier tube further comprises a double walled structure having an outer tube and a concentric inner tube which are connected with each other by means of several radial bridging elements which are uniformly distributed around the circumference so that an inner lumen is formed within the inner tube for insertion of the antenna and a plurality of outer lumena are formed between the inner tube and the outer tube.

3. A flexible medical catheter of claim 2 wherein at least one bridging lumen is formed in the cross-section of at least one of the radial bridging elements.

4. A flexible medical catheter of claim 1 for use with an antenna which radiates microwave energy.

5. A flexible medical catheter of claim 2 wherein any of the of outer lumina formed between the inner tube and the outer tube are used for transporting fluids.

6. A flexible medical catheter of claim 2 wherein any of the of outer lumina formed between the inner tube and the outer tube are used for insertion of measuring and monitoring devices.

* * * * *